(12) United States Patent
Barnikol et al.

(10) Patent No.: US 7,005,414 B2
(45) Date of Patent: *Feb. 28, 2006

(54) SYNTHETIC OXYGEN TRANSPORT MADE FROM CROSS-LINKED MODIFIED HUMAN OR PORCINE HAEMOGLOBIN WITH IMPROVED PROPERTIES, METHOD FOR A PREPARATION THEREOF FROM PURIFIED MATERIAL AND USE THEREOF

(75) Inventors: Wolfgang Barnikol, Mainz (DE); Oswald Burkhard, Kriegsfeld (DE); Harald Pötzschke, Wiesbaden (DE); Ulrike Domack, Nieder-Olm (DE); Stephanie Dinkelmann, Kaiserslautern (DE); Bernd Fiedler, Unna (DE); Birgit Manz, Essen (DE)

(73) Assignee: Sanguibiotech GmbH, Witten (DE)

(*) Notice: Subject to any disclaimer, the term of this patent is extended or adjusted under 35 U.S.C. 154(b) by 0 days.

This patent is subject to a terminal disclaimer.

(21) Appl. No.: 10/312,610
(22) PCT Filed: Jun. 12, 2001
(86) PCT No.: PCT/EP01/06613

§ 371 (c)(1),
(2), (4) Date: Aug. 28, 2003

(87) PCT Pub. No.: WO02/00230
PCT Pub. Date: Jan. 3, 2002

(65) Prior Publication Data
US 2004/0029780 A1 Feb. 12, 2004

(30) Foreign Application Priority Data
Jun. 29, 2000 (DE) .................................... 100 31 740

(51) Int. Cl.
A61K 38/16 (2006.01)

(52) U.S. Cl. ................. 514/6; 530/385; 514/2

(58) Field of Classification Search .............. 514/6, 514/60, 2; 424/529; 530/385; 525/54.1
See application file for complete search history.

(56) References Cited

U.S. PATENT DOCUMENTS

| | | | |
|---|---|---|---|
| 4,001,200 A | 1/1977 | Bonsen et al. ......... 260/112.5 R |
| 4,001,401 A | 1/1977 | Bonsen et al. .............. 424/177 |
| 4,179,637 A | 12/1979 | Santora ...................... 313/316 |
| 4,857,636 A | 8/1989 | Hsia ........................... 530/385 |
| 5,380,824 A | 1/1995 | Marschall et al. .......... 530/385 |
| 5,386,014 A | 1/1995 | Nho et al. ................... 530/385 |
| 5,439,882 A | 8/1995 | Feola et al. .................... 514/6 |
| 5,478,805 A | 12/1995 | Shorr et al. .................... 514/6 |

FOREIGN PATENT DOCUMENTS

| | | |
|---|---|---|
| DE | 449 885 | 9/1927 |
| DE | 0 26 07 706 | 9/1976 |
| DE | 2616 086 | 11/1977 |
| DE | 30 26 398 | 3/1981 |
| DE | 0 31 30 770 | 3/1983 |
| EP | 0 067 029 | 12/1982 |
| EP | 0206 448 | 12/1986 |
| EP | 0 221 618 | 5/1987 |
| EP | 0 854 151 | 7/1998 |
| WO | WO 91/07190 | 5/1991 |
| WO | WO 91/16352 | 10/1991 |

OTHER PUBLICATIONS

XP002182224—Azhigirova M. Alekseevna et al: "Production of artificial oxygen carrier—using a Haemoglobin Solution, Useful in Establishing Erythrocyte Substitute Based on Chemically Modified Haemoglobin", Oct. 2, 1997.

XP-0010337782—Poetzschke H et al: "Molar Masses and Structure in Solution of Haemoglobin Hyper–Polymers—a Common Calibration of Size Exclusion Chromatography of these Artificial Oxygen Carriers" Artificial Cells Blood Substitutes and Immobilization Biotechnology, 25(6), 527–540 (1997).

XP-001029599—Haney Chad R., et al: "Purification and Chemical Modifications of Hemoglobin in Developing Hemoglobin Based Oxygen Carriers" Advanced Drug Delivery Reviews 40 (2000) 153–164.

Fitzgerald, L. R; "Cutaneous Respiration in Man"; Cutaneous Respirtion, Division of Anatomy, University of Tennessee Medical Units, Memphis, TN, Jul. 1957, pp. 325–336, vol. 37.

(Continued)

Primary Examiner—Robert A. Wax
Assistant Examiner—Robert B. Mondesi
(74) Attorney, Agent, or Firm—Norris McLaughlin & Marcus PA (57) ABSTRACT

According to the claims, the present invention comprises the preparation of chemically modified, cross-linked hemoglobins with improved functional properties, the cross-linked hemoglobins prepared according to this method and the use of these hemoglobins as artificial oxygen carriers. The synthesis method is characterized by technical simplicity as well as by high yields.

Deoxygenated hemoglobin of high purity is conjugated covalently under the protection of an antioxidant with an effector of oxygen binding, especially with pyridoxal-5-phosphate, after which the hemoglobin is polymerized with glutardialdehyde as a bifunctional cross-linking agent. At the same time, there is a large increase in the volume of the reaction mixture and a decrease in the concentration of the hemoglobin during the addition of the cross-linking agent. Subsequently, after further dilution with water, a polyethylene oxide derivative is chemically linked to the cross-linked hemoglobins. Polymers are obtained, which are compatible with blood plasma and have optimized cooperativity and half saturation pressure values and can find use as artificial oxygen carriers and, in particular, are divided into a lower molecular weight fraction as blood substitute and a higher molecular weight fraction as blood additive, for example, for the treatment of oxygen-deficiency conditions.

18 Claims, 3 Drawing Sheets

OTHER PUBLICATIONS

Barnikol, W. K.R.et al; "Die Feinstruktur der Sauerstoff–Hämoblogin–Bindung als Hilfsmittel zum Studium pharmakologischer Wirkungen . . . "; Physiologisches Institut der Johannes Guttenberg–Germany, Funkt. Biol. med. 2, (1983), pp. 245–249.

Kothe, N., et al.; "Characterization of a modified, stroma-free hemoglovin solution as an oxygen–carrying plasma substitute"; Scientific Department of Biotest Pharma GmbH, Frankfurt, Germany; Surgery, Gynecology & Obstertrics, Dec. 1985, vol. 161, pp. 563–569.

Bosman, R.J. et al. "Free Polymerized Hemoglobin Versus Hydroxyethyl Starch in Resuscitation of Hypovolemic Dogs", Anesth. Analg. 75, pp. 811–817.

Pabst, R.; "Sauerstofftransport mit stromafreien Hämoglobinlösungen und Fluorocarbonen"; Med. Klin. 72 (1977) pp. 1555–1562, vol. 39.

Chang, T.M.S., "How safe are modified hemoglobins?" Blood Substitutes: Present and Future Perspectives, Elsevier Science, Amsterdam (1998).

Keipert, et al, "Pyridoxylated Polyhemoglobin as a red cell substitute for resuscitation of lethal hemorrhagic shock in conscious rats"; Biomat. Med. Dev. Art. Org. 13 (1&2), pp. 1–15 (1935).

Hirlinger, W.K., et al, "Effects of a Partial Exchange with Fluosol DA 20% on healthy Pig", Anästhesist 31, pp. 660–666 (1982).

Keipert, et al; "Pyridoxylated–polyhemoglobin solution: a low viscosity oxygen–delivering blood replacement fluid with normal oncotic pressure and long–term storage feasibility"; Artificial Cells & Organs Research Centre, Faculty of Medicine, McGill University, Montreal, Canada, pp. 185–197.

Hunt, C.A., et al., "Synthesis and Evaluation of a Protypal Artificial Red Cell", Science, 230: pp. 1165–1168 (1985).

Farmer, M.C.; et al; "Preclinical data and clinical trials with diaspirin cross–linked hemoglobin"; Artificial Red Cells, edited by E. Tsuchida, (1995) John Wiley and Sons pp. 177–185.

Keipert P.E., et al, "Metabolism, Distribution, and Excretion of HbXL: A Nondissociation Interdimerically Crosslinked Hemoglobin with Exceptional Oxygen Offloading Capability", Chang, T.M.S., Geyer R. P.(Eds.): Blood Substitutes, Marcel Dekker, New York (1989).

Chang T.M.S., "Modified Hemoglobin as Red Cell Blood Substitutes", Biomat. Art. Cells, Art. Org. 15(2), pp. 323–328 (1987).

Friedman H.J., et al, "In Vivo Evaluation of Pyridoxylated–Polymerized Hemoglobin Solution", Surg. Gynecol., Obstet.: 159, pp. 429–435 (1984).

Bakker, J.C. et al; "Properties of hemoglobin interdimerically cross–linked with NFPLP"; Biomet. Art. Cells & Immob. Bio., vol. 16, pp. 635–636 (1988).

Barnikol, W.K.R. et al, "Hyperpolymeric Hemoglobins and Artifical Oxygen Carriers. An Innovative Attempt at Medical Development", Therapiewoche 46: pp. 811–815 (1996).

Pötzschke, H. et al; "Vernetzte globuläre proteine—eine neue klasse halbsynthetischer makromoleküle: . . . "; Macromol. Chem. Phys. 197, pp. 1419–1437 (1996).

Barnikol, W.K.R., "the Influence of Glutardialdehyde on the Oxygen Cooperativity of Human Hemoglobin", Pflügers Archi 406: R 61 (1986).

Conover et al, "The ability of polyethylene glycol conjugated bovine hemoglobin (PEG–Hb) to adequately deliver oxygen in both exchange transfusion and top–loaded rat models"; Art. Cells, Blood Subst. Immobil. Biotech. 27: pp. 93–107 (1999).

Looker, D. et al; "A human recombinant haemoglobin designed for use as a blood substitute"; Nature. vol. 356, Mar. 19, 1992; pp. 258–260.

Xue, H. et al; "Preparation of conjugated hemoglobins"; Methods in Enzymology, vol. 231, pp. 308–332 (1994).

Barnikol, W. K. R., et al; "Highly polymerized human haemoglobin as an oxygen–carrying blood substitute", Advances in Experimental Medicine and Biology, vol. 215, pp. 129–134 (1987).

Tam, et al; "Blood replacement in dogs by dextran–hemoglobin"; Can. J. Biochem, vol. 56, (1978); pp. 981–984.

Gould, et al; "The clinical development of human polymerized hemoglobin"; Blood Substitutes: principles, methods, products and clinical trials, edited by Thomas Ming Swi Chang (1998).

Bakker, et al; "Preparation and characterization of crosslinked and polymerized hemoglobin solutions"; Biomat., Art. Cells & Immob. Biotec., 20(2–4), pp. 233–241 (1992).

"Points to consider in the safety evaluation of hemoglobin–based oxygen carriers"; Center for Biologies Evaluation and Research; Transfusion vol. 31, 4 (1991) pp. 369–371.

Pötzschke, H. et al "A novel method for determining molecular weights of widely distributed polymers with the help of gel photography and viscosimetry using hemoglobin hyperpolymers as examples", Macromolecular chemistry and Physics 197, pp. 3229–3250 (1996).

Barnikol, W.K.R. et al, "An improved modification of the micro–method according to the measurement of Niesel and Thews for $O_2$–Hb–binding curves in whole blood and concentrated Hb solutions", Respiration 36, pp. 86–95 (1978).

Sharma et al; "Role of no mechanism in cardiovascular effects of diaspirin cross–linked hemoglobin in anesthetized rats"; American Physiological Society; pp. 1379–1388(1995).

Rohlfs et al; "Arterial blood pressure responses to cell–free hemoglobin solutions and the reaction with nitric oxide"; The Journal of Biological Chemistry, vol. 273, No. 20, Issue of May 15, pp. 12128–12134 (1998).

Rodeberg et al; "Nitric oxide: and overview"; The AmericanJournal of Surgery, vol. 170, Sep. 1995, pp. 292–303.

Vogel, et al; "Coronary constrictor effect of stroma–free hemoglobin solutions"; The American Journal of Physiol., vol. 251; pp. H413–H420 (1986).

Pötzschke, et al; "A new type of artificial oxygen carrier: soluble hyperpolymeric haemoglobin with negligible oncotic pressure—production of thermally stable hyperpolymers from human blood with glutaraldehyde as corss–linker"; Biomat., Art. Cells && Immob. Biotech., 20(2–4), pp. 287–291 (1992).

Pötzschke et al; "Molar masses and structure in solution of haemoglobin hyperpolymers– a common calibration of size exclusion chromatography of these artificial oxygen carriers"; Art. Cells, Blood Subs., and Immob. Biotech., 25(6), pp. 527–540 (1997).

Pearce et al; "Overvies of preclinical and clinical efficacy of biopure's HBOCs"; Blood substitutes: Principles, Methods, Products and Clinical Trials, edited by Thomas Ming Swi Chang (1998) Chapter 5.

Pötzschke, et al; "Divinyl sulfone cross–linked hyperpolymeric human haemoglobin as an artifical oxyen carrier in anaesthetized spontaneously breathing rats"; Oxygen transport to tissue XV, edited by P. Vaupel, et al, Plenum Press, New York (1994) pp. 205–213.

SYNTHETIC OXYGEN TRANSPORT MADE FROM CROSS-LINKED MODIFIED HUMAN OR PORCINE HAEMOGLOBIN WITH IMPROVED PROPERTIES, METHOD FOR A PREPARATION THEREOF FROM PURIFIED MATERIAL AND USE THEREOF

This application is a 371 of PCT/EP01/06613, filed on Jun. 12, 2001.

In accordance with the claims, the present invention comprises the production of chemically modified, cross-linked hemoglobins with improved functional properties, the cross-linked hemoglobins produced by this method and their use as artificial oxygen carriers. The production method is characterized by its technical simplicity as well as by high yields.

Deoxygenated hemoglobin of high purity is conjugated covalently under the protection of an antioxidant with an effector for oxygen bonding, especially with pyridoxal-5-phosphate. After that, and the hemoglobin is polymerized with glutardialdehyde with a very large increase in the volume of the reaction mixture and, accordingly, a very great dilution of the reactants during the addition of the cross-linking agent. Subsequently, after dilution with water, a polyethylene oxide derivative is linked chemically to the cross-linked hemoglobins. Polymers with optimized oxygen-binding characteristics are obtained, which are compatible with blood plasma and, especially when divided into a low molecular weight and a high molecular weight fraction, can be used as artificial oxygen carriers as a blood substitute or blood additive, for example, for the treatment of oxygen deficiency conditions.

For various clinical indications in medicine, it is desirable to have available an artificial support system for the transport of oxygen. In the event of an acute loss of blood, it is not only appropriate to replace the liquid volume isotonically and isoncotically, but also to restore a further essential function of the blood, namely the transport of oxygen. With the decreasing preparedness to donate blood, adequate supplies of blood are available less and less in the event of an acute catastrophe or in the event of a war, particularly for covering an unforeseeable demand. The instantaneous availability of suitable supplies of blood furthermore is associated with appreciable logistic problems. Moreover, blood can usually be stored for only about 35 days and must therefore be constantly replenished. This creates appreciable costs. On the other hand, artificial solutions can be kept for a significantly longer time, since they may optionally be frozen. Depending on the storage time, stored blood acidifies intracellularly. As a result, its acute oxygen binding characteristics are not by any means optimum and must be regenerated once again in the organism. On the other hand, an artificial oxygen carrier functions optimally from the first instant. The increasing lack of preparedness to donate blood is contrasted, on the other hand, by the increase in demand of an aging population. At the same time, because of the aging of the population, the number of potential blood donors has decreased. Likewise, because of unpredictable risks of infection (immune weakness, hepatitis), the population of the slums is unavailable as blood donors. An artificial, oxygen-transporting blood replacement would also be universal and independent of the blood group. Moreover, it is possible that a volume deficiency shock can be counteracted more rapidly with such a blood replacement than with stored blood, since the erythrocytes in the stored blood have stiffened and therefore have a lower capillary permeability. In any case, animal experiments have shown that a volume deficiency shock can be combated more effectively with an oxygen-transporting blood replacement than with simple plasma expanders (Pabst, R. (1977): "Oxygen Transport with Stroma-free Hemoglobin Solutions and Fluorocarbons", Med. Klin. 72: 1555–1562, Keipert, P. E., Chang, T. M. S (1985): "Pyridoxylated Polyhemogloblin as a Red Cell Substitute for Resuscitation of Lethal Hemorrhagic Shock in Conscious Rats: Biomater., Med. Dev., Artif. Organs 13: 1–15). There are other applications for an artificial oxygen carrier, such as complicated surgical interventions, which necessarily are associated with high blood losses and can be carried out less and less, because of a lack of appropriate stored blood. On the other hand, larger and more invasive surgical interventions, including also transplants, are constantly being developed. In a particular case, the possibility of carrying out such an intervention depends decisively on the availability of a sufficient number of suitable stored bloods. Moreover, organs, which are to be transplanted, can be preserved far better, if they are perfused with (artificial) oxygen carriers. For instance, a liver transplant requires up to 100 transfusion units of 450 mL each. In cases of polytraumatic injuries, such as those caused by an automobile accident, similarly large amounts are required.

However, there is a need for an artificial oxygen-transporting, blood additive not only in the case of an acute loss of blood, but also in the case of chronic blood-circulation disorders (especially cerebral, coronary, renal and peripheral—such as a sudden loss of hearing—or an anemic crisis, such as in the case of chronic osteomyelitis or after tumor chemotherapy). The use of the additive is also an option in order to prevent a threatening abortion in the case of a fetal oxygen deficiency due to a placenta insufficiency or to prevent oxygen-deficiency injuries during birth. A requirement of this type is even significantly greater than that in the aforementioned case of an acute blood loss. Such chronic circulation disorders are the cause of death of about 750,000 people annually in Germany. In addition, there are the cases of illness that arise from this cause. On the other hand, only about half that number of people die from cancer every year. It is well known that attempts are made to treat chronic oxygen deficiencies in tissues by supplying hyperbaric oxygen. Aside from the fact that this treatment is effective only as long as the oxygen overpressure exists and the procedure is not harmless, the danger of oxidative damage to tissue due to reactions of free radicals of oxygen, which can be detected by corresponding reaction products, exists here. An artificial oxygen carrier acts as long as it is present and offers so-called low-pressure oxygen to the tissue, so that the aforementioned damage does not occur.

The use of the oxygen-transporting blood additives as a temporary support for the endogenous oxygen transport system offers a further possibility and alternative for combating a chronic tissue deficiency of oxygen, the treatment of which was previously attempted with circulation-promoting means, such as vessel dilators.

The fact that it is a functional oxygen treatment is very much to the benefit of the concept. It is not the substrate (the oxygen) that is improved; instead, the function of the carrier system, which brings the oxygen to the tissue is improved. This makes the treatment multiplicative in its effect and, with that, very effective and gives it, at the same time, a catalytic character. In addition, there are clear indications that an oxygen carrier, which is dissolved in plasma, is far more effective than one, which is "packed" in erythrocytes.

Moreover, such an artificial blood replacement can be produced free of known pathogens; infection problems, such as hepatitis and acquired immune deficiency (AIDS) are avoided in this manner.

An additional potential group of recipients for artificial oxygen-transporting solutions are patients, for whom an allergic reaction, for example, to HLA antigens, may be expected. Until now, the removal of leukocytes from stored blood by filtration through cotton has been attempted. On the other hand, artificial blood replacement solutions would be completely free of leukocytes. Recently, it has been observed in pigs that, after an improvement in the oxygen supply (decrease in the oxygen affinity of the hemoglobin), the cardiac output of the heart is decreased while the heart rate remains unaffected (Vilereal M. C., et al. (1987): "Engineered Red Blood Cells with Modified Oxygen-Transport Properties: A New Oxygen Carrier", Biomater., Med. Dev., Artif. Organs 15: 397). In a different paper (Bosman, R. J., et al. (1992): "Free Polymerized Hemoglobin Versus Hydroxyethyl Starch in Resuscitation of Hypovolemic Dogs", Anesth. Analg. 75: 811–817", it was shown that the administration of oxygen-transporting solutions after a volume deficiency shock in dogs prevented the increase in the cardiac output and accordingly is easy on the heart. By improving the oxygen supply, the possibility arises of achieving a functional cardiac protection, which is helpful, for example, in the case of an infarction. This would be a completely new aspect of the use of oxygen-transporting solutions.

A further use of such artificial oxygen carriers would be to increase in the radiation sensitivity of tumors, especially since there are increasing indications that molecular oxygen carriers, dissolved in the plasma, deliver the oxygen to the tissue far more effectively than does whole blood. Such artificial carriers bring about a synergism with the native (intraerythrocytic) carrier. In other words, the molecularly dispersed artificial carrier in the blood plasma not only per se is best at giving off oxygen from the capillary, but also intensifies the oxygen delivery of the existing native system by way of the mechanism of facilitated diffusion. This means that only a very low concentration of the artificial carrier in the plasma is required for this purpose. Nevertheless, this functional therapy (see above) remains extremely effective.

Everything, which has been stated, makes clear the need for an artificial oxygen transporter. It is indispensable for the use of an artificial oxygen carrier that its starting material is available in sufficient amounts. Deteriorated stored blood accordingly does not solve the problem. It is therefore necessary to use animal hemoglobins, preferably from the most important slaughtered animals, namely cattle and/or pigs.

Roughly two types of applications arise from the presentation of the need for artificial oxygen carriers, on the one hand, in the case of a heavy loss of blood and, on the other, in the case of a chronic oxygen deficiency. In the first case, an iso-oncotic, oxygen transporting volume substitute (artificial oxygen carrier of the first generation) is required as compensation and on the other hand, in the second case, an oxygen-transporting blood additive (artificial oxygen carrier of a second and new generation) is required. As already mentioned, the latter case is far more frequent. Moreover, an appropriate blood additive, in combination with so-called plasma expander, also permits an acute loss of blood to be treated with the great advantage that the physician has the possibility of coordinating the administration of oxygen carriers as well as the liquid volume with the requirements with the individual patient.

The organism is also able to change both (the amount of oxygen carrier and the blood volume) independently of one another, namely the erythrocyte formation by way of the erythropoetin and the plasma volume by way of its own regulation system. The two parameters are uncoupled owing to the fact that the carrier has a much smaller colloidal osmotic pressure than does the plasma.

Previously, three basically different strategies for developing an artificial oxygen carrier for blood were employed by others (state of the art: Rudolph, A. S. et al. (Publisher) Red Blood Cell Substitutes: Basic Principles and Clinical Applications, Marcel Dekker, New York, et al., 1998; Tsuchida E. (Publisher): Blood Substitutes: Present and Future Perspectives, Elsevier Science, Amsterdam, 1998; Chang, T. M. S. (Author & Publisher) Blood Substitutes: Principles, Methods, Products and Clinical Trials, Volume 1 and Volume 2, Karger Landes, Basel et al. 1997 and 1998).

The use of emulsions with fluorinated hydrocarbons—recently, other halogens, such as bromine, have also been used—in which oxygen is particularly soluble (Hirlinger, W. K., et al. (1982): Effects of a Partial Blood Exchange with Fluosol DA 20% on the intact organism of the pig", An̈asthesist 31 660–666). However, since the fluorinated hydrocarbons are lipophilic, it is to be expected that interactions and disorders in the lipid layers of the cell membrane will occur. The later are integrating, functional components of the cell. Moreover, the fluorinated hydrocarbons must be disposed with emulsifiers, such as phospholipids, which can interfere additionally with the membranes of the cells (so-called artificial oxygen carriers, based on fluorinated hydrocarbons of the first generation).

A further strategy is represented by the microencapsulation of highly concentrated solutions of natural and also of chemically modified hemoglobins in phospholipid vesicles with addition of suitable effectors of hemoglobin binding ("artificial erythrocytes or hemosomes") (Ogata Y. (1994): "Characteristics of Neo Red Cells, Their Function and Safety: In-Vivo Studies", Artificial Cells, Blood Substitutes, and Immobilization Biotechnologies 22: 875–881). The first animal experiments in this field have been successful (Hunt, C. A. et al. (1985): "Synthesis and Evaluation of a Protypal Artificial Red Cell", Science 230: 1165–1168). The vesicles had a diameter of less than 0.05 $\mu$m and their volume therefore was more than two powers of ten smaller than that of natural red blood cells.

The third strategy consists of the production of infusible hemoglobin solutions. The artificial oxygen carrier then occurs extracellularly in the blood. The first two solutions of the problem can be regarded as relating to the production of an artificial blood, so that the difficulty of a colloidal, osmotic interference cannot occur. On the other hand, for this solution of the problem, there was a plasma expander at the very start, the macromolecules of which can also transport oxygen (a so-called, artificial oxygen carrier), on the basis of hemoglobin of the first generation.

Native hemoglobin cannot be used for this purpose, for example, because it is eliminated too rapidly by way of the kidneys. A chemical modification therefore is indispensable. For example, within the scope of this strategy, hemoglobin has been bound by its amino groups covalently to dextrans or has itself been polymerized to a molecular weight of 700,000 g/mole. The former procedure was pursued, for example, by Firma Fresenius (Fresenium E. (1976), Blood and Plasma Substitute—Comprising a Colloidal Solution of Hydroxyethyl Starch Coupled to Hemoglobin-Free Stroma", Patent DE-P 2616-086) and the later by Firma Biotest (Bonhard K., et al. (1983): "Method for Obtaining Hepatitis-Safe, Sterile, Pyrogen-Free and Stroma-Free Hemoglobin Solutions", Patent DE-O 31 30 770) and Firma Alza (Bonsen P. (1976): "Water-soluble Polymerized Hemoglobin", Patent DE-O 26 07 706). A further strategy with regard to extracellular solutions is the stabilization of hemoglobin by cross-linking it to an intratetramer or by appending side groups (oligo ethylene glycol) without significantly increasing the molecular weight of the tetramer (stabilized hemoglobins (Matsushita M. et al. (1987): "In Vivo Evaluation of Pyridoxylated Hemoglobin-Polyoxythene Conjugate", Biomat, Artif. Cells. Artif. Org. 15: 377). As mentioned above, extracellular blood replacement solutions have given promising results with respect to treatment of shock in animal experiments.

The use of hemoglobin as an artificial oxygen carrier has an advantage over the use of fluorinated hydrocarbons, because the advantageous properties of the natural binding of oxygen can be utilized. These include the optimally adapted oxygen affinity, the homotropic cooperativity, that is, the S-shape of the oxygen binding curve, as well as the (alkaline) drilling effect which forms the basis of a natural, self-regulatory mechanism for the selective delivery of oxygen to deficiently supplied tissue.

It is clearly evident from the relevant literature that an intra-tetrameric, covalent bonding of hemoglobin units (Keipert P. E., et al. (1989): "Metabolism, Distribution, and Excretion of HbXL: A Nondissociation Interdimerically Crosslinked Hemoglobin with Exceptional Oxygen Offloading Capability",—in: Change, T. M. S., Geyer R. P. (Eds.): Blood Substitutes, Marcel Dekker, New York 1989) and/or a polymerization of the hemoglobin leads to a large increase in the residence time in the blood. (Chang T. M. S. (1987): "Modified Hemoglobin as Red Cell Blood Substitutes", Biomater., Med. Devices Artif. Organs 14: 323–328; Friedman H. J., et al. (1984): "In Vivo Evaluation of Pyridoxylated-Polymerized Hemoglobin Solution", Surg. Gynecol., Obstet.: 159 429–435). This is an essential prerequisite for the clinical usefulness of such solutions.

However, in the case of extracellular, molecularly disposed artificial oxygen carriers, a very large area of need, the chronic oxygen deficiency, has been ignored by aiming for iso-oncotic solutions. As already mentioned, the significantly more frequently occurring consequences of chronic circulation disorders can, however, be improved only by oxygen-transporting solutions, the colloidal osmotic pressure of which can be disregarded with respect to the normal (35 mbar), that is, only with the help of an oxygen-transporting blood additive, a "molecular erythrocytes concentrate", as it were. These are artificial oxygen carriers based on hemoglobin of a second generation.

The following problems arose during the different attempts to develop an artificial oxygen transporter:

Increase in the hemoglobin affinity for oxygen: due to the chemical modification of the hemoglobin molecule, the half saturation pressure (P50) is decreased. As a result, the delivery of oxygen to the tissue is made more difficult. This occurs in a pronounced manner during the binding of hemoglobin to dextran. In order to avoid the increase in oxygen affinity, suitable effectors (such as pyridoxal phosphate) have been linked to the prosthetic group of the hemoglobin.

Frequently, the so-called n50 value (HILL index) as an expression of the decreased homotropic cooperativity (weakened S shape of the oxygen-hemoglobin binding curve), is decreased at the same time; this also makes it more difficult to supply the tissue with oxygen. This S shape of the oxygen-hemoglobin binding curve at the same time facilitates the absorption of oxygen in the lung and its delivery to the cells. On the other hand, fluorinated hydrocarbons have a linear "oxygen binding curve" and therefore do not have this functional advantage.

The artificial oxygen carrier frequently has too short a residence time in the organism, the dissolved hemoglobins being eliminated by way of the kidneys. In the case of extracellular hemoglobin solutions as artificial oxygen carriers, the attempt has been made to prevent the elimination by intermolecular cross-linking; nevertheless, the residence time of the extracellular hemoglobins remain shorter than desired. On the other hand, hemosomes are removed from the plasma by the reticuloendothelial system of the organism. For example, the half life of the artificial erythrocytes (see above) was 5.8 hours.

Excessive colloidal osmotic pressure: This can result in a loss of volume (volume deficiency shock). This effect occurs when the molecular weight of the artificial oxygen carrier is comparable to that of the plasma proteins. As a result, the dosage of the artificial oxygen carrier cannot be chosen freely and, instead, the oncotic relationships must be taken into consideration.

The oncotic milieu of the plasma continues to be determined primarily by the so-called second virial coefficient ($A_2$ value). This characterizes the interaction of the (always macromolecular) oxygen carrier with the solvent (water). The synthesis should be conducted so that this value is close to zero.

Excessive viscosity of the carrier solution: Usually, this is associated with an $A_2$ value, which is too large, and it occurs preferably when a carrier consists of chain molecules. According to the Einstein viscosity law, an excessive viscosity does not occur if the polymeric carrier molecules are spherical and compact.

In vitro stability of the carrier molecules: This refers, on the one hand, to the decomposition of the molecules and, on the other, to the oxidative binding of methemoglobin, which is no longer capable of binding oxygen, and finally to the viscosity due to the slowly changing interactions between the carrier and the albumin of the plasma.

Excessive reaction of the reticuloendothelial system (RES): The main influencing factor is the molecular size of the artificial carrier. The critical limit for this is about 0.3 $\mu$m. Larger particles activate the RES.

Kidney and liver damage: a kidney shock occurs especially if the stroma-containing hemoglobin solution is used. Ever since the solutions were subjected to ultrafiltration, kidney damage has no longer being observed. Liver damage was indicated with the help of the plasma transaminase mirror; it is presumably based on cellular membrane interactions: the liver has an open flow path (fenestrated capillaries).

Hemostasis must also be checked: disorders in the sense of preventing and inhibiting hemostasis are conceivable; special attention must be paid to thrombocyte aggregation.

Antigenic effects: In this connection, it was recently shown in homolog experiments in rats that native hemoglobin has no antigenic activity and that the polymerization with glutardialehyde has not increased the antigenicity (Hertzman, C. M., et al. (1986): "Serum Antibody Titers in Rats Receiving Repeated Small Subcutaneous Injections of Hemoglobin or Polyhemoglobin: A Preliminary Report", Int. J. Artif. Organs 9: 179–182). In the same paper it is shown that native and polymerized human hemoglobin has little antigenic activity in rats and that the effect is intensified at most slightly by polymerization.

Toxic effects can be differentiated as pyrogenic, vasoconstrictive—for example, on coronary vessels—and endotoxic. The vasoconstrictive effect is based presumably on entrapping nitrogen monoxide radicals, which are, and is well known, endogenous, vasodilatoric control substances; however, the vasoconstrictive effect can also be explained by the high effectiveness of the artificial carrier, in that the smooth musculature is supplied "too well" with oxygen.

In vivo stability: An endogenous, enzymatic degradation, for example, by proteases, must be considered.

Overloading the organism with lipoids (emulsifiers): this complication occurs only when microencapsulated hemoglobin solutions of fluorinated hydrocarbons are used; a complement activation by way of the alternative path as well as antibody formation was noted here.

Compatibility of the artificial carriers with fresh, human blood plasma, there may be precipitation, depending on the pH.

Presumably, because of the problems listed here, an artificial oxygen carrier is as yet not available for routine clinical applications. It is evident from the various problems named that a usable artificial oxygen carrier must still satisfy a larger range of requirements.

In nature, oxygen is always transported in microscopic giant aggregates. Two basically different "problem solutions" have been developed here. In the case of higher animals (and also in man), the molecular oxygen carrier is packed in cells (in the erythrocytes). Secondly, oxygen-binding giant molecules develop, which are dissolved extracellularly in a hemolymph and not intracellularly. This variation is encountered predominantly in lower elements to different degrees. Annelides, for example, have high molecular weight hemoglobins, averaging about three million g/mole, as oxygen carrier. Furthermore, there are so-called hemerythins, for which the iron, as oxygen binder, is released molecularly directly with the protein. Finally, there are the hemocyanins with a molecular weight of about eight million g/mole, for which copper is the oxygen-binding heavy metal ion (see also Barnikol, W. K. R., et al. (1996): "Hyperpolymeric Hemoglobins and Artificial Oxygen Carriers. An Innovative Attempt at Medical Development", Therapiewoche 46: 811–815). The historical transition from extracellular dissolved oxygen carriers to the erythrocytes has caused an increase in the oxygen content of the blood fluid by a factor of three. For example, 1 mL of the "blood" of the earthworm can bind at most 3.6 μmoles of oxygen. On the other hand, up to 9.0 μmoles of oxygen are bound in the same volume of human blood.

The earthworm has giant molecules (erythrocruorin) in its blood as oxygen carrier with a molecular weight of about 3,400,000 g/moles and approximately 200 binding sites for oxygen. Moreover, the molecule is very compact and its quaternary structure is highly ordered. The molecule is so large, that it can be made visible directly with the help of the electron microscope. Its concentration in the hemolymph is at least 6 g/dL. Measuring the oxygen-binding curve under simulated in vivo conditions gives a half saturation pressure (P50) of 9.1 torr (Barnikol, W. K. R. and O. Burkard (1987): "Highly Polymerized Human Hemoglobin as an Oxygen-Carrying Blood Substitute", Advances in Experimental Medicine and Biology, vol. 215: 129–134; Barnikol, W. K. R. (1986) "The Influence of Glutardialdehyde on the Oxygen Cooperativity of Human Hemoglobin", Pflügers Archiv 406: R 61). This system thus supplies the cells of the earthworm adequately with oxygen. Due to the extremely high molecular weight, the hemoglobin of the earthworm has practically no colloidal osmotic effect anymore (only about 0.4 mbar). With that, as in the blood of mammals—the oncotic pressure of the erythrocytes is only $10^{-7}$ torr—the two functions of colloid osmolarity and oxygen binding are uncoupled and both can be varied freely as control variables of the organism.

If the principle of the earthworm system is to be transferred to artificial oxygen carriers, which are based on human or animal hemoglobin, the hemoglobin molecule must be changed so that, as extracellular giant molecule with a negligible oncotic pressure, it can support the normal oxygen transport of the erythrocyte at least intermittently. Such artificial oxygen carriers then are highly polymerized hemoglobins, which must take into account all the problems mentioned above. Earthworm "hemoglobin", which admittedly fulfills the oncotic pressure requirement, will not be usable for man for this purpose, because it presumably has too high an antigenicity; moreover, the half-saturation pressure of 9 torr is too low (Barnikol, W. K. R and O. Burkard (1987): "Highly Polymerized Human Hemoglobin as an Oxygen-Carrying Blood Substitute", Advances in Experimental Medicine and Biology, vol. 215: 129–134; Barnikol, W. K. R. (1986): "The Influence of Glutardialdyde on the Oxygen Cooperativity of Human Hemoglobin", Pflügers Archiv 406: R 61). Moreover, it can presumably not be obtained in the amounts required.

Until now, in the development of artificial oxygen carriers, attempts were made to adjust the half saturation pressure of the carriers precisely to the normal value of about 20 torr in man. However, animal experiments showed that a molecularly disperse artificial oxygen carrier with a half saturation pressure of about 15 torr oxygenates organs best (Conover et al. (1999), Art. Cells, Blood Subst. Immobil. Biotech. 27: 93–107). On the other hand, however, animal experiments also show that a sufficiently large oxygen capacity of the blood is at least equally important for an adequate oxygen supply (Moss, G. S., et al (1984): "Hemoglobin Solution—From Tetramer Polymers", In: The Red Cell: Sixth Aven. Arbor Conference, Alan R. Riss, N.Y., 1984: 191–210). In turn, this depends on the possible concentration of the oxygen carrier in the plasma. Furthermore, it was shown here that it is not necessary to adhere to a half saturation pressure of 26 torr. Rather, it is essential that a certain critical value must be exceeded.

It is a further requirement of the development of an artificial oxygen carrier that a manufacturing process be as simple as possible and, with that, economic, especially since it is necessary to work under sterile conditions from the start. The yield of the product should be high and material for use as blood additive and material for use as oxygen-transporting blood-volume substitutes should be formed simultaneously during the cross-linking reaction.

Furthermore, during the production of the artificial polymers from hemoglobin by linking the hemoglobin molecules over their amino groups by means of suitable, bifunctional cross-linking agents, particular attention must be paid to the fact that molecular networks, which are insoluble and therefore decrease the yield, are not formed. For this reason, the formation of the so-called percolation distribution of the molecular weight is to be prevented.

It is therefore an object of the present invention to be able to produce hypo-oncotic, artificial oxygen carriers from cross-linked hemoglobins, which have optimized, good functional properties, especially the characteristics of oxygen binding, and are suitable for use as pharmaceutical products in man, in a technically simple process in a large yield.

Pursuant to the invention, this objective is accomplished as described below. Surprisingly, it was possible eliminate the fundamental problem of the formation of a percolation distribution of the multimerization degrees and molecular weights by the cross-linking of the polyfunctional hemoglobins with the bifunctional cross-linking agent, glutardialdehyde, by greatly increasing the volume of the reaction mixture (2- to 10-fold in all) during the cross-linking, and, moreover, adding initially the cross-linker as a dilute solution and subsequently additionally diluting with water. By these means, cross-linked hemoglobins with a high degree of cross-linking are formed in a large yield, without developing a percolation distribution of the molecular weight and forming insoluble, molecular networks. Rather, the crude product of the cross-linking is distinguished by a certain, desirable (approximate) upper limit of the molecular weight range. A so-called quadrilateral distribution of the molecular weight is obtained in the gel chromatogram (see FIGS. 1, 2 and 3).

The inventive preparation thus comprises the following steps:

In a one-vessel reaction, hemoglobin i) initially is deoxygenated, especially by passing nitrogen over it, ii) subsequently reacted covalently with a chemically reactive effector of the oxygen binding, iii) after which the solution is treated with a chemically unreactive effector and then iv) the hemogloblin is cross-linked stably and covalently with glutardialdehyde with a very great dilution (2- to 5-fold of the volume of the reaction mixture, with simultaneous addition of the cross-linker (in solution)) and subsequently the reaction volume is increased further with water, the total dilution of the solution being 2- to 10-fold, especially 2- to 7-fold and particularly 5- to 6-fold and then v) a polyethylene oxide is linked covalently.

The product obtained can be worked up by known methods.

Preferably, the starting hemoglobin originates from pigs or from man, pigs and especially domestic pigs being particularly preferred.

Particularly and pursuant to the invention, the glutardialdehyde is added in step iii) in a very highly diluted solution in a time-controlled manner. Preferably, there is a subsequent further dilution with water and an increase in the reaction volume, so that the above-mentioned total dilution is achieved.

Moreover, in step iv), glutardialdehyde is preferably added in a molar amount of 6 to 10 and especially of 7 to 9 moles/mole, based on the monomeric hemoglobin, dissolved in 1–4, preferably 1–2, particularly 1.5–2 and especially 1.7–1.9 L of water per liter of original reaction solution.

This addition is timed to take place between about 3 and 15, especially between 3 and 10 and particularly between 4 and 6 minutes. Subsequently, the solution is reacted for 1 to 6 hours.

It is furthermore preferred that, before the reaction of step ii), 2–8, especially 3–6 and particularly 3–4 moles of sodium ascorbate per mole of uncrosslinked hemoglobin be added to the solution containing the hemoglobin. This reaction takes place over a period of 0.5 to 6 hours and especially of 70 to 120 minutes.

Furthermore, in step ii), preferably pyridoxal-5'-phosphate is linked as effector in a molar ratio, based on the monomeric hemoglobin, of 0.5 to 3, preferably of 1 to 2.5 moles/mole covalently over a period of 0.5 to 20 and especially of 1 to 7 hours.

Pursuant to the invention, and furthermore preferably and advantageously, reductive sodium borohydride is added in step ii) as well as in step iv) after the covalent linking of pyridoxal-5'-phosphate and of glutardialdehyde.

This is added particularly in step ii) in an amount of 1 to 9, preferably of 1 to 5 and particularly of 1 to 2.5 moles/mole, for example, over a period of 30 to 90 minutes, and in step iv) in an amount of 5 to 20 and especially of 6 to 12 moles/mole, in each case based on the monomeric hemoglobin, over a period of 15 to 100 minutes.

It is particularly preferred if, as unreactive effector in step iii), 2,3-bisphosphoglycerate is added in an amount of 0.5 to 6 and especially of 1 to 4 moles/mole, based on the monomeric hemoglobin, and if about 5 to 50 minutes, especially 10 to 20 minutes and particularly 15 minutes thereafter glutardialdehyde is added.

As polyethylene oxide, preferably a polyethylene glycol ether with, for example, a C1–C5 alkyl group, such as methyl, ethyl and butyl, with a molecular weight of 500 to 3000 g/mole, especially a methoxy-polyethylene glycol derivative with a molecular weight of 1500 to 2500 g/mole and especially of 2000 g/mole, such as, especially, methoxypolyethylene glycol succinimidyl propionate, in amounts of 2 to 12 and especially 3 to 8 moles/mole of hemoglobin. Other derivatizing products are methoxypolyethylene glycol succinimidyl succinamide and methoxy-polyethylene glycol succinimidyl hydroxyacetate. The linking of polyalkylene oxide to uncrosslinked hemoglobin is described in U.S. Pat. Nos. 4,179,637, 5,478,805 and 5,386,014 and the EP-A 0 206 448, EP-A 0 067 029 and the DE OS 3,026,398.

The reaction is carried preferably over 1 to 4 and particularly over 2 to 3 hours.

It is furthermore advantageous that all synthesis reactions take place, in particular, in solutions freed from oxygen by tonometry with oxygen-free gases. The method used is described by H. Potzschke in "Hyperpolymers of Human Hemoglobin, Development of Preparative Methods for their Synthesis, Validation of Analytical Methods and Equipment for their Characterization", Dissertation, Medical Faculty, University of Vienna, 1997.

The product obtained can be worked up in the usual manner, as described in the following. In particular, it has a molecular weight distribution of 50,000 to 5,000,000 and optionally up to 10,000,000 g/moles or more.

Preferably, the product obtained can be divided into a fraction of high average molecular weight and a fraction of low average molecular weight, the boundary preferably being at 700,000 g/moles, by a preparative, material-separating method, such as a preparative volume exclusion chromatography, an ultrafiltration, a fractional precipitation, for example, with polyalkylene oxide or salt such as ammonium sulfate as precipitant, or a field-flow fractionation method (Curling, J. M (publisher), "Methods of Plasma Protein Fractionation", Academic Press, London et al. 1980, as well as the patents EP-A 0 854 151 and EP-A 95 107 280).

A pharmaceutical preparation can be produced from the product of high molecular weight and also from the product of low molecular weight, a parenteral blood substitute being obtained from the low molecular fraction of the polymers and a parenteral blood additive from the high molecular weight fraction of the polymers.

Before (and after) the individual steps of the reaction, the pH is adjusted preferably with lactic acid or sodium hydroxide solution to values between 6 and 10, depending on the reaction step, for example, to a value of 6.5 to 7.5 before step ii), subsequently to 7.5 to 8.5 and subsequently again to 6.5 to 7.5 before step iii), after that to 7.5 to 9, as well as to 7.5 to 10 before step v).

The concentration of hemoglobin preferably is 200 to 380 g/L and particularly 240 to 360 g/L; the solution furthermore contains 10 to 150 mmoles/L of sodium bicarbonate and 10 to 150 mmoles/L of sodium chloride.

During the "one-vessel reaction", the temperature is 2° to 42° C., especially 3° to 25° C. and particularly 4° to 24° C.

The artificial oxygen carrier, produced pursuant to the invention, preferably has an n50 value (cooperativity) of 1.6 to 2.5 and a p50 value (semi-saturation pressure) of 16 to 24 torr.

The product, which is obtained pursuant to the invention and has the characteristics given, can be used to produce an agent for an intravasal or biomedical application as an artificial oxygen carrier, or in the form of a pharmaceutical preparation as a blood substitute or as an additive to blood to increase the oxygen transport capacity (blood additive) or to a nutrient solution in human and animal organisms, in individual organs or in biotechnical applications, especially for the treatment of a chronic oxygen deficiency in man.

To prepare the products, which are to be administered, the inventive hemoglobin derivatives are dissolved in suitable media, such as infusion solutions, for example in aqueous salt or glucose solutions, preferably in concentrations isotonic with the blood plasma.

The inventive method is based accordingly on individual reaction steps, which are matched to one another and the significance and effects of which are explained in the following.

The starting material is a very pure hemoglobin. This may be obtained by known methods from the fresh blood of slaughtered animals or, for example, overaged stored blood. Methods for obtaining purified hemoglobins are described by Antonini, E. et al. (publisher) in: "Hemoglobin"? (Colowick, S. P. and N. O. Kaplan (publishers): Methods in Enzymology, Vol. 76) Academic Press, New York et al. 1981.

As mentioned, pursuant to the invention, during the cross-linking with glutardialdehyde, which is known (DE 24 99 885, U.S. Pat. Nos. 4,857,636, 4,001,200, 4,001,401 and DE 449 885, U.S. Pat. No. 5,439,882, EP A 0 221 618), the hemoglobin is deoxygenated (that is, freed from its physiological ligands, oxygen), because only polymers, which are prepared from hemoglobin that is deoxygenated during the cross-linking have the oxygen binding properties, which enable them to be used as artificial oxygen carriers for the desired indications. Preferably, as further protection against oxidation of the hemoglobin by traces of remaining oxygen, the latter can be removed by chemical reaction with ascorbate ions.

Especially pyridoxal-5'-phosphate is linked as effector of the oxygen binding in an amount, optimized for the functional properties of the end product, covalently to the pig or human hemoglobin. This linking of pyridoxal-5'-phosphate to hemoglobins basically is known; for example, patent EP-P 0 528 841 describes a method for the synthesis of pyridoxylated hemoglobin. The pyridoxylation leads to the desired half-saturation pressure value if the inventive procedure is employed.

The linking sites (aldimines=Schiffs bases) of the unstable covalent linkage of pyridoxal-5'-phosphate can be stabilized, as is well known (see above), by reduction with sodium borohydride (amines are formed), the aforementioned special conditions being adhered to pursuant to the invention. The capability of hemoglobin molecules for homotropic cooperativity of the oxygen binding sites with one another is generally clearly lost by cross-linking the hemoglobin with the cross-linking agent, glutardialdehyde.

Pursuant to the invention, and to maintain this capability, 2,3-bisphosphoglycerate, a "heterotropic", chemically not reactive effector of the oxygen binding of the hemoglobin, is added before the cross-linking. Accordingly, this 2,3-bisphosphoglycerate can be added reversibly to its binding site in the hemoglobin molecule during the cross-linking. After the synthesis, 2,3-bisphosphoglycerate, together with unused reactants as well as excess reaction product, is removed completely (see below).

Glutardialdehyde is used as bifunctional cross-linking agent under the inventive conditions given above.

Two cross-linking sites (aldimines=Schiffs bases) of the cross-linked molecular glutardialdehyde bonds are stabilized, as described, by reduction with sodium borohydride (amines are formed), the inventive conditions being observed.

Cross-linked hemoglobins are formed by the cross-linking and have a molecular weight distribution between about 50,000 and 5,000,000 g/mole (and larger, for example, 10,000,000 to 15,000,000 g/mole).

To improve the compatibility with plasma proteins, a polyethylene oxide (MW) derivative, especially the above-mentioned, monofunctional, activated (methoxy) polyethylene glycol having a molecular weight of 1,500 to 2,500 g/mole, is linked to the cross-linked hemoglobin. The linking of polyethylene glycol (PEG), the so-called pegylation, to as well as the cross-linking of hemoglobins is known (see also E. Tsucheda (Publisher); Blood Substitutes; Present and Future Perspectives, Elsevier Science, Amsterdam 1998).

However, the pegylation, as well as the cross-linking of hemoglobins together, as well as the use of the chemically inactive effector before the cross-linking, which contributes particularly to obtaining cooperativity as well as, in particular, the cross-linking conditions described, are new. The anyhow weak reaction of the RES and also the enzymatic degradation by proteases are prevented by the pegylation carried out here.

The pH is adjusted as described above.

On the one hand, the development of a percolation distribution can be prevented by the inventive dilution and by the reaction sequence and conditions obtained. On the other hand, undesirable changes in the oxygen affinity and cooperativity can be avoided by the cross-linking of and covalent attachment to hemoglobin by, for example, glutardialdehyde, pyridoxal phosphate and polyethylene oxide and, in particular, a high plasma compatibility can also be achieved.

All reaction steps together contribute to these special properties of the product produced pursuant to the invention.

The further working up is within the scope of knowledge of someone skilled in the art. Insoluble components can be removed by centrifugation (for example, for 20 minutes with a relative centrifugal acceleration of 20,000 g). The cross-linked hemoglobins are divided by a "well known" preparative step of the process, especially by a volume exclusion chromatography or ultrafiltration, a factional precipitation or a field flow fractionation into a higher molecular weight and a lower molecular weight fraction. If suitable methods are selected, (for example, the nominal molecular-weight separation boundary of the ultrafiltration membrane or the molecular weight separation range of the gel used are particularly important), the unused reactants as well as the undesirable reaction products are removed at the same time.

A particularly preferred embodiment of the invention is explained in greater detail by means of the following preparation example.

Purified pig or human hemoglobin, with a concentration between 200 and 380 g/L and preferably between 240 and 360 g/L, is dissolved in an aqueous electrolyte. The latter contain sodium hydrogen carbonate at a concentration between 10 and 150 mmoles/L and preferably between 40 and 60 mmoles/L, and sodium chloride at a concentration of between 10 and 150 moles/L and preferably between 50 and 100 mmoles per L. The temperature is 2° to 42° C. and preferably between 3° and 25° C. The hemoglobin solution is stirred and pure nitrogen is passed over it in order to deoxygenate the hemoglobin. To this solution, 2 to 8 moles and preferably 3 to 4 moles of sodium ascorbate (as a 1 molar solution in water) are added per mole of hemoglobin and allowed to react for a period between 0.5 and 6 hours and preferably between 70 and 120 minutes.

The pH of the solution is now adjusted to a value between 6.5 and 7.5 and preferably between 6.9 and 7.3 with lactic acid or sodium hydroxide solution having a concentration between 0.1 and 1 and preferably between 0.4 and 0.6 moles/L. Pyridoxal-5'-phosphate (0.5 to 3.0 and preferably from 1.0 to 2.5 moles per mole of hemoglobin) is now added and allowed to react between 0.5 and 20 and preferably between 1 and 7 hours.

The pH is now adjusted with sodium hydroxide solution or lactic acid, having a concentration between 0.1 and 1 and preferably between 0.4 and 0.6 moles/L to a value between 7.5 and 8.5 and preferably between 7.7 and 8.2.

Now, 1.0 to 9.0 and preferably 1.0 to 2.5 moles of sodium borohydride (as a 1-molar solution in 0.01 molar sodium hydroxide solution) are added and allowed to react for between 30 and 90 and preferably for between 50 and 70 minutes The pH of the solution is adjusted with lactic acid or sodium hydroxide solution, having a concentration between 0.1 and 1 and preferably between 0.4 and 0.6 moles/L) to a value between 6.5 and 7.5 and preferably between 6.9 and 7.5

Now, 0.5 to 6.0 and preferably 1.0 to 4.0 moles of 2,3-bisphosphoglycerate per mole of hemoglobin are added and allowed to react for between 5 and 50 and preferably for between 10 and 20 minutes.

Subsequently, the time-controlled addition of the bifunctional cross-linking agent is made. Between 6 and 10 and preferably between 7 and 9 moles of glutardialdehyde per mole of hemoglobin, dissolved in 1 to 4 and preferably 1.5 to 2 L of water per 1 of hemoglobin solution, are added within 3 to 10 and preferably within 4 to 6 minutes and allowed to react for between 1 and 6 and preferably for between 2 and 3 hours.

The pH is adjusted with sodium hydroxide or lactic acid, having a concentration between 0.1 and 1 and preferably between 0.4 and 0.6 moles/L, to a value between 7.5 and 9.0 and preferably between 7.6 and 8.8.

In all, 5 to 20 and preferably 6 to 12 moles of sodium borohydride (as a 1-molar solution in 0.01 molar sodium hydroxide solution) is added per mole of hemoglobin and allowed to react for between 15 and 100 and preferably between 30 and 80 minutes. This is followed by the addition of 0 to 4 and preferably between 0.5 and 3 L of water per liter of the original hemoglobin solution.

If necessary, the pH is adjusted with sodium hydroxide solution or lactic acid, having a concentration between 0.1 and 1 and preferably between 0.4 and 0.6 moles/L to a value between 7.5 and 10 and preferably between 8 and 9. Preferably, between 3 and 8 moles of an activated polyethylene oxide derivative, preferably methoxy-succinimidyl propionate polyethylene glycol, with a molecular weight between 500 and 3000, preferably 1000 and 2500 and particularly 2000 g/mole are now added per mole of monomeric hemoglobin.

Subsequently, while continuing to stir the hemoglobin solution, the nitrogen atmosphere is replaced for 1 to 3 hours by pure oxygen and the hemoglobin thus is oxygenated swiftly. The working up is carried out as described above.

The advantages of the inventive method can be summarized as follow.

Due to the inventive reaction sequence, especially the increase in the reaction volume in step iv) of the method, a product is obtained, which can be used completely for the preparation of artificial oxygen carriers. Moreover, about half of the product can be used as a blood additive (the fraction with the cross-linked hemoglobins of higher degrees of polymerization, fraction I) and as blood volume substitute (fraction II), with the low molecular weight fractions. The separation can be accomplished easily with known methods, some possible methods being, for example, listed in the patents EP-A 95 107 280 and EP-A 97 100 790. The polymers of fraction I, preferably up to a molecular weight of more than 700,000 g/mole, are so adequately uniform on a molecular basis, that they have an adequately low colloidal osmotic pressure in the desirably therapeutic plasma concentration. A small viral coefficient as well as a low viscosity are achieved by this molecular uniformity. The comparability of the proteins of the blood plasma, the sufficiently large immune compatibility and intravasal residence time, as well as adequately low vasoconstrictive side effects, that is, a low extravasation, of the polymers of fraction I is achieved by a covalent linkage of the polyalkylene oxides. Moreover, the requirement of simplicity and economic efficiency is taken into account in a decisive manner by this new method in that the whole preparation takes place in a single vessel (a so-called one-vessel preparation) and in high yields of more than 70%, the yield of polymers with a molecular weight of more than 700,000 g/mole exceeding 15%.

The method makes it possible to prepare modified and cross-linked hemoglobins in a few process steps. The process parameters selected lead to a defined distribution of modified hemoglobin polymers, which, as artificial oxygen carriers, suitably take into account also the physiological circumstances in the blood serum.

Moreover, the cooperativity of the uncrossed-link hemoglobin in the cross-linked product is largely obtained and the half saturation pressure can be adjusted suitably.

In parenteral application, the artificial oxygen carriers, produced pursuant to the invention from cross-linked hemoglobin, are compatible with the plasma and can be employed clinically as described.

The invention is described in greater detail by means of the following examples, FIGS. 1 to 3 showing the following.

Furthermore, the following analytical methods were employed.

1. The hemoglobin contents were determined photometrically with the modified cyanhemoglobin method of Drabkin ("Hemoglobin Color Test MRP 3", Boehrimger Mannheim, Germany).

2. pH values were measured potentiometrically (glass electrode) with a blood-gas analyzer ("ABL 5", Radiometer, Willich, Germany)

3. The molecular weight distribution of the cross-linked hemoglobins was determined by volume-exclusion chromatography (Pötzschke H. et al. (1996): "Cross-linked Globular Proteins—A new class of semi-synthetic polymeric molecules: characterization of their structure and solution in solution by means of volume-exclusion chromatography, viscosimetry, osmometry and light scattering using hyperpolymeric hemoglobins and mycoglobins as example", Macromolecular Chemistry and Physics 197, 1419–1437, as well as Pötzschke H. et al. (1996): "A novel method for determining molecular weights of widely distributed polymers with the help of gel photography and viscosimetry using hemoglobin hyperpolymers as examples", Macromolecular Chemistry and Physics 197, 3229–3250) on Sephacryl S-400 HR gel (Pharmacia Biotech, Freiburg, Germany).

4. The characteristics of oxygen binding by hemoglobins were determined by means of our own methods and equipment (as described in Barnikol W. K. R. et al. (1978): "An improved modification of the Niesel and Thews micromethod for measuring $O_2$—Hb-binding curves in whole blood and concentrated Hb solutions", Respiration 36, 86–95).

5. The Plasma compatibility of cross-linked hemoglobins was investigated by means of a standardized in vitro precipitation test (Domack, U. (1997), "Development and in vivo evaluation of an artificial oxygen carrier on the basis of bovine hemoglobin", dissertation Chemistry Department of the Johannes Gutenberg University, Mainz 1997): Hemoglobin solutions (with hemoglobin contents of about 30 g/L in an aqueous electrolyte (StLg) containing 125 mM of sodium chloride, 4.5 mM of potassium chloride and 3 mM of sodium nitride) were mixed with equal amounts of freshly obtained, sterile filtered, human plasma. Subsequently, up to 20 µL of a 0.5 molar lactic acid was added to in each case 500 µL of the mixture and mixed in, so that for each hemoglobin derivative, which was to be investigated, the pH ranged from 7.4 to 6.8. After an incubation period of 30 minutes at room temperature and centrifugation of the samples, the hemoglobin content was determined as a measure of the hemoglobin, which had not been precipitated, and the associated pH in the supernatant was determined. In addition, a subjective, visual check for colorless precipitate of plasma proteins was conducted.

EXAMPLE 1

Preparation of an Inventive Cross-Linked and Molecularly Modified Pig Hemoglobin at 4° C. by the General Method of Preparation Pig hemoglobin of high purity, dissolved in a concentration of 330 g/L in an aqueous electrolyte containing 50 mM of sodium bicarbonate and 100 mM of sodium chloride, was deoxygenated at 4° C. by stirring the solution under pure nitrogen, which was constantly being renewed. Subsequently, 4 moles of sodium ascorbate (as a I-molar solution in water) was added per mole of (monomeric) hemoglobin and allowed to react for 6 hours. The pH of the solution was adjusted to a value of 7.1 with 0.5-molar lactic acid. Subsequently, 1.1 mole of pyridoxal-5'-phosphate were added per mole of hemoglobin and allowed to react for 16 hours. The pH of the solution was now adjusted to a value of 7.8 with 0.5 molar sodium hydroxide solution and 1.1 moles of sodium borohydride (as a 1-molar solution in 0.01-molar sodium hydroxide solution) were added and allowed to react for 1 hour. The pH was now adjusted to a value of 7.3 with 0.5-molar lactic acid. Initially, 1.1 moles of 2,3-bisphosphoglycerate per mole of hemoglobin and, after a reaction period of 15 minutes, 8 moles of glutardialdehyde per mole of hemoglobin, dissolved in 1.8 L of pure water, was added per liter of hemoglobin solution for cross-linking the hemoglobin within 5 minutes and allowed to react for 2.5 hours. After the pH was adjusted to a value of 7.8 with a 0.5 molar sodium hydroxide solution, 15 moles of sodium borohydride (as a 1-molar solution in 0.01 molar sodium hydroxide solution) were added per mole of hemoglobin for 1 hour. Subsequently, 2 L of water were added per liter of original hemoglobin solution. The pH then was 9.3. Immediately thereafter, 4 moles of methoxysuccinimidyl propionate polyethylene glycol having a molecular weight of 2,000 g/mole were added over a period of 2 hours. The nitrogen atmosphere over the solution was replaced by pure oxygen.

After 1 hour, the insoluble constituents were removed by centrifuging (20.000 g for 15 minutes). Subsequently, the electrolyte was changed by a volume exclusion chromatography (Sephadex G-25 gel, Pharmacia, Germany) to an aqueous electrolyte solution containing 125 mM of sodium chloride, 4.5 mM of potassium chloride and 20 mM of sodium bicarbonate.

The yield was 77%; the yield for a molecular weight greater than 700,000 g/mole is 28%.

Figure 1:
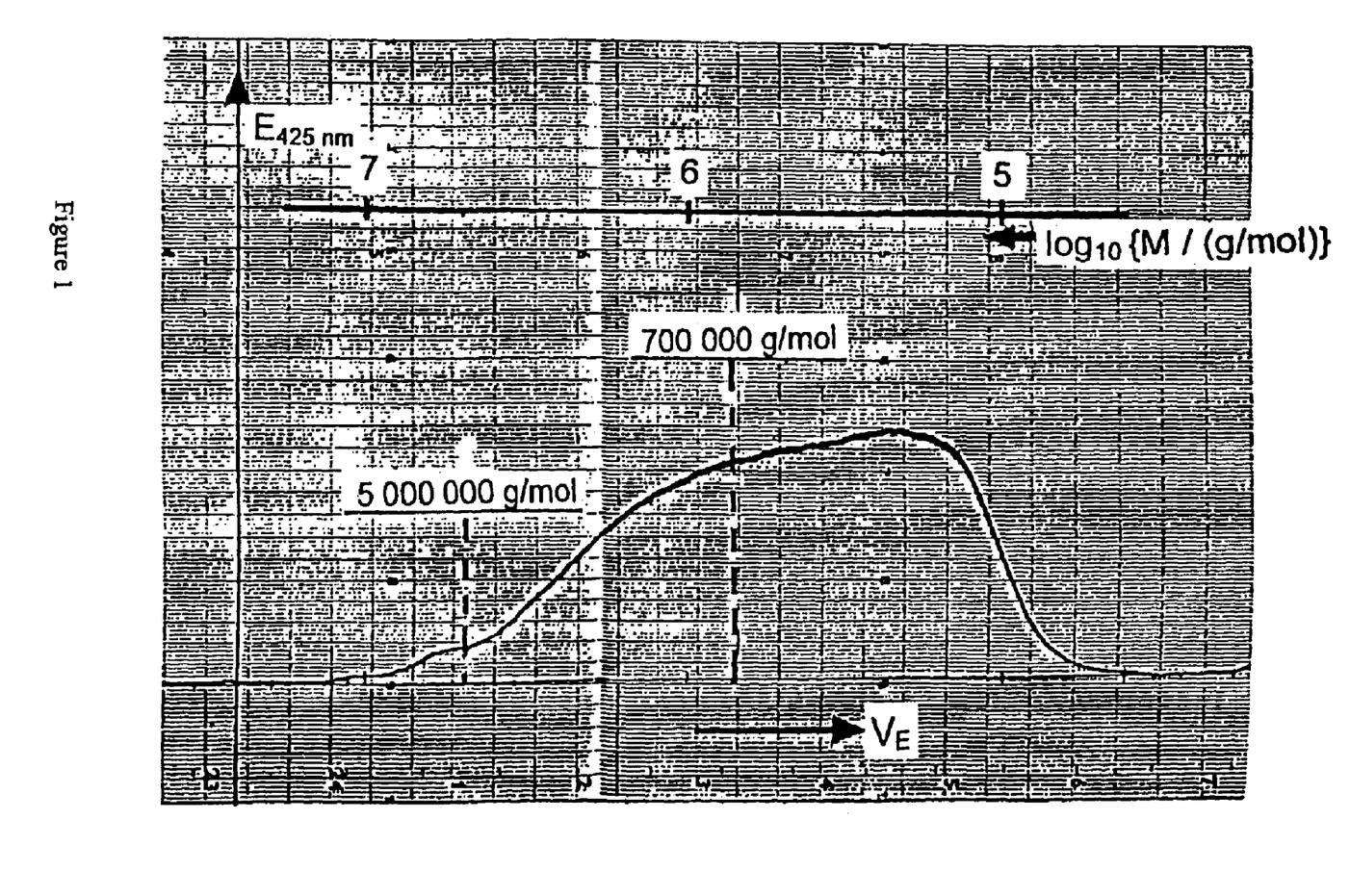
FIG. 1 shows a mass average distribution of the molecular sizes and molecular weights (M) of the pig hemoglobin polymers of Example 1, shown as a volume exclusion chromatogram, obtained with a Sephacryl S-400 HR gel, Pharmacia, Freiburg, Germany. $E_{425\ nm}$ is the extinction in the chromatography eluate. The abscissa values of 700,000 and 5,000,000 g/mole are shown.

FIG. 1 shows a representation of the distribution of the molar masses of the hemoglobin polymers obtained in the form of a volume exclusion chromatogram.

Measurements of the characteristic of the oxygen binding under physiological conditions (a temperature of 37° C., a carbon dioxide partial pressure of 40 torr and a pH of 7.4) reveal that the product had a p50 value of 22 torr and an n50 value of 1.95.

In the "precipitation test", the cross-linked pig hemoglobin, in the pH range of 7.4 to 6.8, showed no interactions whatsoever with human plasma, especially no detectable precipitates of the hemoglobin or of the plasma proteins.

EXAMPLE 2

Preparation of an Inventive Cross-Linked and Molecularly Modified Pig Hemoglobin at Room Temperature by the General Method of Preparation Pig hemoglobin of high purity, dissolved in a concentration of 330 g/L in an aqueous electrolyte containing 50 mM of sodium bicarbonate and 100 mM of sodium chloride, was deoxygenated at 22° C. by stirring the solution under pure nitrogen, which was constantly being renewed. Subsequently, 4 moles of sodium ascorbate (as a 1-molar solution in water) was added per mole of (monomeric) hemoglobin and allowed to react for 90 minutes, the pH of the solution was adjusted to a value of 7.1 with 0.5-molar lactic acid. Subsequently, 1.1 moles of pyridoxal-5'-phosphate were added per mole of hemoglobin and allowed to react for 2 hours. The pH of the solution was now adjusted to a value of 7.8 with 0.5 molar sodium hydroxide solution and 1.5 moles of sodium borohydride (as a 1-molar solution in 0.01-molar sodium hydroxide solution) were added and allowed to react for 1 hour. The pH was now adjusted to a value of 7.3 with 0.5-molar lactic acid. Initially, 1.5 moles of 2,3-bisphosphoglycerate per mole of hemoglobin and, after a reaction period of 15 minutes, 9 moles of glutardialdehyde per mole of hemoglobin, dissolved in 1.8 L of pure water, was added per liter of hemoglobin solution within 5 minutes, for cross-linking the hemoglobin and allowed to react for 1 hour. After the pH was adjusted to a value of 7.8 with a 0.5 molar sodium hydroxide solution, 10 moles of sodium borohydride (as a 1-molar solution in 0.01 molar sodium hydroxide solution) were added per mole of hemoglobin for 30 minutes. The pH was 8.7. Immediately thereafter, 8 moles of methoxysuccinimidyl propionate polyethylene glycol having a molecular weight of 1000 g/mole, were added over a period of 1 hour. The nitrogen atmosphere over the solution was replaced with pure oxygen.

After 1 hour, the insoluble constituents were removed by centrifuging (20.000 g for 10 minutes). Subsequently, the electrolyte was changed by volume exclusion chromatography (Sephadex G-25 gel, Pharmacia, Germany) to an aqueous electrolyte solution containing 125 mM of sodium chloride, 4.5 mM of potassium chloride and 20 mM of sodium bicarbonate.

The yield was 79%; the yield for a molecular weight greater than 700,000 μmole was 28%.

Figure 2:
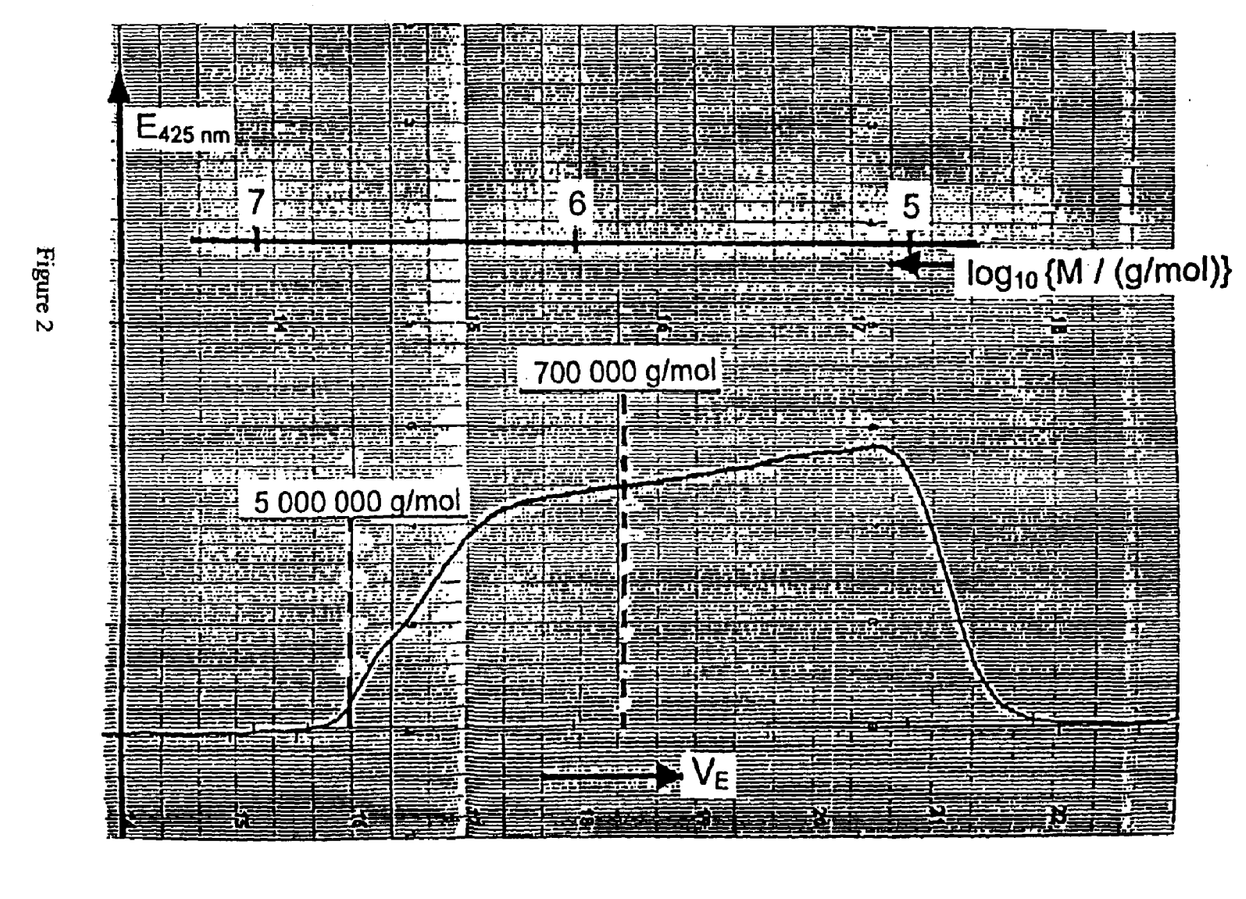
FIG. 2 shows a chromatogram for Example 2, the explanations being given in FIG. 1.

FIG. 2 shows a representation of the distribution of the molar masses of the hemoglobin polymers obtained in the form of a volume exclusion chromatogram.

Measurements of the characteristic of the oxygen binding under physiological conditions (a temperature of 37° C., a carbon dioxide partial pressure of 40 torr and a pH of 7.4) reveal that the product had a p50 value of 22 torr and an n50 value of 1.6.

In the "precipitation test", the cross-linked pig hemoglobin, in the physiologically and pathophysiologically interesting pH range of 7.4 to 6.8, showed no interactions whatsoever with human plasma, especially no detectible precipitates of the hemoglobin or the plasma proteins.

EXAMPLE 3

Preparation of an Inventive Cross-Linked and Molecularly Modified Human Hemoglobin at 4° C. by the General Method of Preparation Human hemoglobin of high purity, dissolved in a concentration of 330 g/L in an aqueous electrolyte containing 50 mM of sodium bicarbonate and 100 mM of sodium chloride, was deoxygenated at 4° C. by stirring the solution under pure nitrogen, which was constantly being renewed. Subsequently, 4 moles of sodium ascorbate (as a 1-molar solution in water) was added per mole of (monomeric) hemoglobin and allowed to react for 3 hours. The pH of the solution was adjusted to a value of 7.1 with 0.5-molar lactic acid. Subsequently, 1.1 mole of pyridoxal-5'-phosphate were added per mole of hemoglobin and allowed to react for 16 hours. The pH of the solution was now adjusted to a value of 7.8 with 0.5 molar sodium hydroxide solution and 1.1 moles of sodium borohydride (as a 1-molar solution in 0.01-molar sodium hydroxide solution) were added and allowed to react for 1 hour. The pH was now adjusted to a value of 7.3 with 0.5-molar lactic acid. Initially, 1.5 moles of 2,3-bisphosphoglycerate per mole of hemoglobin and, after a reaction period of 15 minutes, 9 moles of glutardialdehyde per mole of hemoglobin, dissolved in 1.8 L of pure water, were added uniformly within 5 minutes per liter of hemoglobin solution for cross-linking the hemoglobin and allowed to react for 2.5 hours. After the pH was adjusted to a value of 8.0 with a 0.5 molar sodium hydroxide solution, 10 moles of sodium borohydride (as a 1-molar solution in 0.01 molar sodium hydroxide solution) were added per mole of hemoglobin for 1 hour. Subsequently, 2 L of water were added per liter of original hemoglobin solution. The pH then was 8.6. Immediately thereafter, 4 moles of methoxysuccinimidyl propionate polyethylene glycol, having a molecular weight of 2000 g/mole, was added over a period of 2 hours. The nitrogen atmosphere over the solution was replaced with pure oxygen.

After 1 hour, the insoluble constituents were removed by centrifuging (20.000 g for 10 minutes). Subsequently, the electrolyte was changed by a volume exclusion chromatography (Sephadex G-25 gel, Pharmacia, Germany) to an aqueous electrolyte solution containing 125 mM of sodium chloride, 4.5 mM of potassium chloride and 20 mM of sodium bicarbonate.

Figure 3:
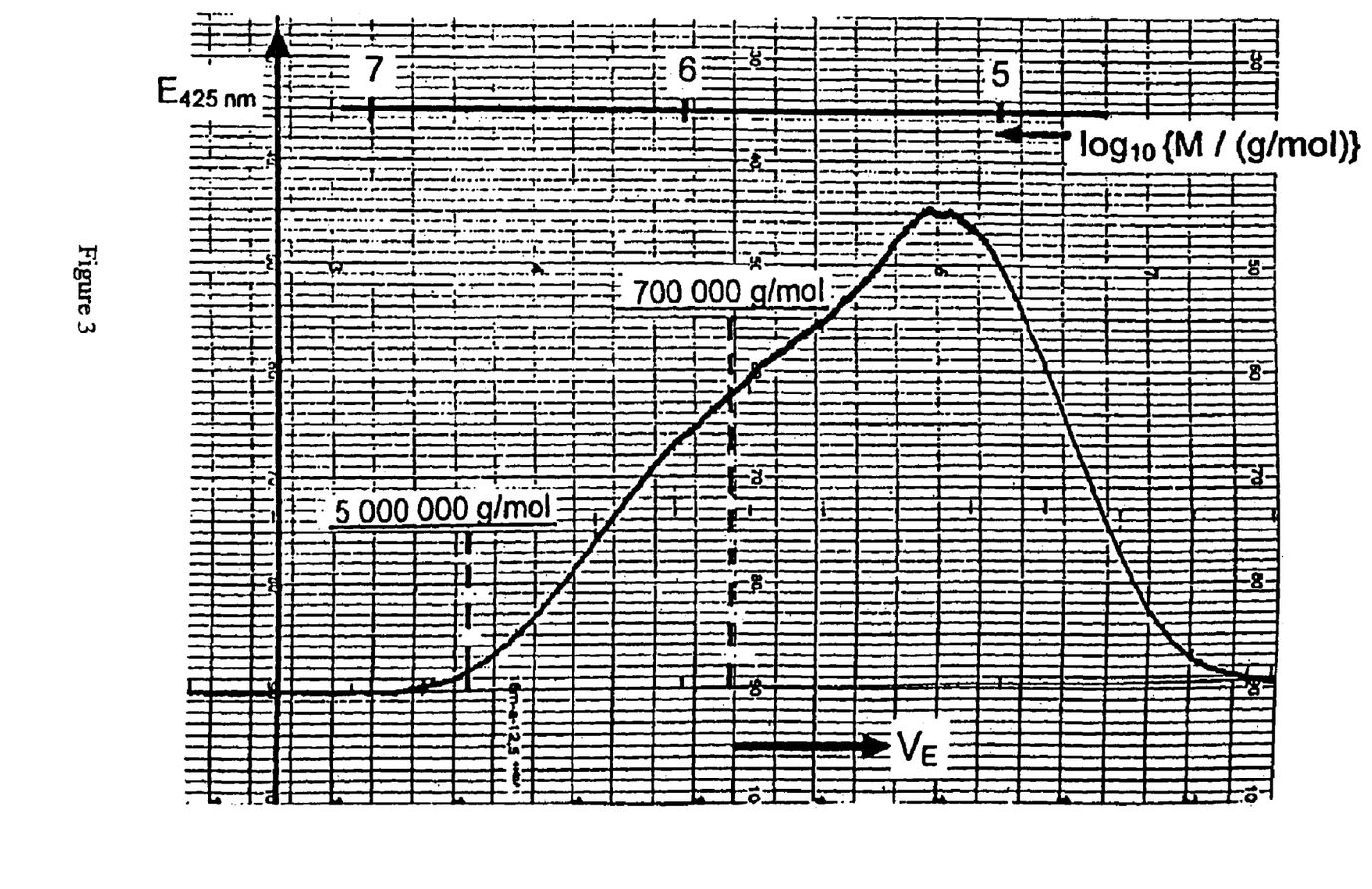
FIG. 3 shows a chromatogram for Example 3, the explanations being given in FIG. 1.

FIG. 3 shows a representation of the distribution of the molar masses of the hemoglobin polymers obtained in the form of a volume exclusion chromatogram.

The total yield was 75%; the yield of polymers with a molecular weight greater than 700,000 g/mole was 17%.

Measurements of the characteristic of the oxygen binding under physiological conditions (a temperature of 37° C., a carbon dioxide partial pressure of 40 torr and a pH of 7.4 reveal that the product had a p50 value (as a measure of the average oxygen affinity) of 21 torr and an n50 value (an average apparent cooperativity of the oxygen binding sites) of 1.74.

In the "precipitation test", the cross-linked pig hemoglobin, in the physiologically and pathophysiologically interesting pH range of 7.4 to 6.8, showed no interactions whatsoever with human plasma, especially no detectible precipitates of the hemoglobin or of plasma proteins.

what is claimed is:

1. Method for the production of artificial oxygen carriers comprising crosslinked hemoglobin, said method comprising the following steps:

i) deoxygenizing a first solution comprising hemoglobin to form a second solution comprising deoxygenated hemoglobin;

ii) covalently reacting the second solution comprising deoxygenated hemoglobin with a chemically reactive effector of an oxygen bonding to form a third solution;

iii) treating the third solution with a non-chemically reactive effector of an oxygen bonding to form a fourth solution; and then iv) stably covalently crosslinking the hemoglobin with glutaraldehyde by diluting the fourth solution and adding a crosslinking agent, then further diluting the fourth solution, while the volume of the fourth solution increases overall by a factor of 2 to 10; and then v) covalently linking a polyethylene oxide derivative to the hemoglobin; and vi) processing and formulating a resulting product as a pharmaceutical.

2. Method according to claim 1, wherein the hemoglobin originates from pigs or human beings.

3. Method according to claim 2, wherein the hemoglobin originates from pigs.

4. Method according to claim 1, wherein in step iv) glutaraldehyde is added to the hemoglobin solution while diluting the hemoglobin solution up to 5- to 6-fold under time control.

5. Method according to claim 4, wherein in step iv) the hemoglobin is monomeric hemoglobin, and glutaraldehyde is added within 3–15 minutes in an amount of 6–10 mol, with respect to the monomeric hemoglobin, dissolved in 1–2 liters of water per liter of original reaction solution, and reacted for another 1–6 hours.

6. Method according to claim 1, wherein to the first solution comprising the hemoglobin, before step ii), there is added 2 to 8 mol sodium ascorbate per mol of uncrosslinked hemoglobin for 0.5–6 hours.

7. Method according to claim 1, wherein in step ii) the hemoglobin is monomeric hemoglobin, the chemically reactive effector of an oxygen bonding is pyridoxal-5'-phosphate, and the pyridoxal-5'-phosphate is covalently bonded onto the monomeric hemoglobin in a molar ratio, with respect to the monomeric hemoglobin, of 0.5 to 3 mol/mol within 0.5 to 20 hours.

8. Method according to claim 7, wherein in steps ii) and iv), after the covalent bonding of pyridoxal-5'-phosphate onto the monomeric hemoglobin, and after covalent crosslinking of the monomeric hemoglobin with glutaraldehyde, reductive sodium borohydride is added in each case.

9. Method according to claim 1, wherein in step iii) the hemoglobin is monomeric hemoglobin, the non-chemically reactive effector of an oxygen bonding is 2,3-bisphosphoglycerate, and the 2,3-bisphosphoglycerate is added in a relative amount of 0.5–6 mol with respect to the monomeric hemoglobin, and step iv) is started 5 to 50 minutes thereafter.

10. Method according to claim 1, wherein in step v), the polyethylene oxide derivative is a polyethylene glycol ester with a molecular weight of 500 to 3000 g/mol.

11. Method according to claim 1, wherein the product obtained is separated by a preparative separating process into a fraction of greater average molecular mass and a fraction of lower average molecular mass.

12. Method according to claim 11, wherein a parenteral blood substitute is prepared from the low molecular weight fraction and a parenteral blood additive is prepared from the higher molecular weight fraction.

13. Artificial oxygen carrier which is a hemoglobin crosslinked and polymerized with glutaraldehyde and covalently linked with a polyethylene oxide derivative.

14. Artificial oxygen carrier according to claim 13, wherein the carrier has an n50 value of 1.6 to 2.5 and a p50 value of 16 to 24 Torr.

15. Method of using an artificial oxygen carrier according to claim 13 for intravascular or biomedical application as a synthetic oxygen carrier, said method comprising administering said artificial oxygen carrier to a patient in need thereof.

16. Method according to claim 15, which comprises administering the artificial oxygen carrier to the patient in need thereof as a substitute for blood (blood substitute) or as an additive to the blood to increase the oxygen transport capacity (blood additive) or in a nutrient solution.

17. Method according to claim 16, which is carried out for the treatment of chronic oxygen deficiency in a human being.

18. Method according to claim 7, wherein in step ii) the hemoglobin is monomeric hemoglobin, the chemically reactive effector of an oxygen bonding is pyridoxal-5'-phosphate, and the pyridoxal-5'-phosphate is covalently bonded onto the monomeric hemoglobin in a molar ratio, with respect to the monomeric hemoglobin, of 1 to 2.5 mol/mol within 0.5 to 20 hours.

* * * * *